(12) United States Patent
Petty

(10) Patent No.: US 9,593,289 B2
(45) Date of Patent: Mar. 14, 2017

(54) CORROSION INHIBITING HYDRAULIC FLUID ADDITIVE

(71) Applicant: Jon A. Petty, Saint George, UT (US)

(72) Inventor: Jon A. Petty, Saint George, UT (US)

(73) Assignee: Jon A. Petty, St. George, UT (US)

( * ) Notice: Subject to any disclaimer, the term of this patent is extended or adjusted under 35 U.S.C. 154(b) by 0 days.

(21) Appl. No.: 14/630,117

(22) Filed: Feb. 24, 2015

(65) Prior Publication Data

US 2016/0244688 A1 Aug. 25, 2016

(51) Int. Cl.
| | | |
|---|---|---|
| *C23F 11/14* | (2006.01) | |
| *G01N 21/78* | (2006.01) | |
| *C10M 133/44* | (2006.01) | |
| *G01N 21/80* | (2006.01) | |
| *C10M 169/04* | (2006.01) | |
| *B60T 17/18* | (2006.01) | |
| *B60T 17/22* | (2006.01) | |
| *G01N 17/04* | (2006.01) | |
| *G01N 21/29* | (2006.01) | |
| *G01N 21/84* | (2006.01) | |
| *C23F 11/00* | (2006.01) | |
| *G01N 21/77* | (2006.01) | |
| *C10M 133/28* | (2006.01) | |

(52) U.S. Cl.
CPC ........... *C10M 133/44* (2013.01); *B60T 17/18* (2013.01); *B60T 17/221* (2013.01); *C10M 169/04* (2013.01); *C23F 11/00* (2013.01); *C23F 11/149* (2013.01); *G01N 17/04* (2013.01); *G01N 21/293* (2013.01); *G01N 21/78* (2013.01); *G01N 21/80* (2013.01); *G01N 21/8483* (2013.01); *C10M 133/28* (2013.01); *C10M 2215/223* (2013.01); *C10N 2230/12* (2013.01); *C10N 2240/08* (2013.01); *G01N 21/29* (2013.01); *G01N 2021/7759* (2013.01)

(58) Field of Classification Search
CPC ... C10M 133/44; C10M 133/28; B60T 17/22; C23F 11/14; C23F 11/148
See application file for complete search history.

(56) References Cited

U.S. PATENT DOCUMENTS

| | | | |
|---|---|---|---|
| 3,338,835 A | | 8/1967 | Wright |
| 3,347,796 A | | 10/1967 | Doelling |
| 3,637,507 A | * | 1/1972 | Gentit .................. C10M 129/18 252/396 |
| 3,992,312 A | * | 11/1976 | Genjida ............... C10M 173/02 252/77 |
| 4,005,023 A | | 1/1977 | Brown, Jr. |
| 4,181,619 A | | 1/1980 | Schmitt |
| 4,209,414 A | * | 6/1980 | Holgado .................. C10M 3/00 252/75 |

(Continued)

FOREIGN PATENT DOCUMENTS

| | | |
|---|---|---|
| CA | 2496921 | 9/2013 |
| WO | WO2013171052 A1 | 11/2013 |

*Primary Examiner* — Paul Hyun
(74) *Attorney, Agent, or Firm* — David Meibos; Maywood IP Law

(57) ABSTRACT

Corrosion inhibiting hydraulic fluid additives, kits, and methods are disclosed. The hydraulic fluid additive may be adapted for use with brake fluid in vehicular brake systems. The kits may include an additive, a hydraulic fluid tester, and/or correlated information on test results and hydraulic fluid service actions.

17 Claims, 9 Drawing Sheets

(56) References Cited

U.S. PATENT DOCUMENTS

| | | | |
|---|---|---|---|
| 4,332,689 A * | 6/1982 | Tanizaki | C10M 173/02 252/79 |
| 4,340,495 A | 7/1982 | Brown, Jr. | |
| 4,689,201 A * | 8/1987 | Longworth | C23F 11/08 252/389.52 |
| 5,425,573 A * | 6/1995 | Mirlocca | B60T 8/42 138/30 |
| 5,700,765 A * | 12/1997 | Barnes | C10M 141/10 252/73 |
| 5,817,605 A | 10/1998 | Papay | |
| 6,074,992 A | 6/2000 | Levesque | |
| 6,558,569 B1 | 5/2003 | Shannon | |
| 7,179,769 B2 | 2/2007 | Sunkara | |
| 7,553,801 B2 | 6/2009 | Alexander | |
| 7,687,442 B2 | 3/2010 | Walton | |
| 7,968,504 B2 | 6/2011 | Mosier | |
| 8,486,878 B2 | 7/2013 | Li Pi Shan | |
| 2002/0129644 A1 * | 9/2002 | Petty | G01N 21/293 73/61.46 |
| 2006/0264337 A1 * | 11/2006 | Wenderoth | C10M 111/02 508/136 |
| 2009/0054282 A1 | 2/2009 | Sunkara | |
| 2010/0107741 A1 * | 5/2010 | Petty | G01N 31/22 73/61.43 |

* cited by examiner

Brake Fluid Corrosion test: Commercial Brake Fluid

Method: FMVSS-116, Para S6.6

| Metal | Initial Wt | Final Wt | Wt Change | Area (sq. cm.) | Wt Change (mg/sq.cm.) | Av. Wt Change (mg/sq.cm.) | Requirement (mg/sq.cm.) | Comments Wt Loss | Appearance |
|---|---|---|---|---|---|---|---|---|---|
| Tinned Iron | | | | | | | | | |
| 1 | 1.9865 | 1.9862 | 0.0003 | 21.5 | 0.00 | 0.00 | <1 | Passes | No Change |
| 2 | 1.8874 | 1.8865 | 0.0009 | 21.5 | 0.00 | | | Passes | No change |
| Steel | | | | | | | | | |
| 1 | 21.8742 | 21.8737 | 0.0005 | 25.1 | 0.00 | 0.00 | <1 | Passes | No change |
| 2 | 20.4571 | 20.4561 | 0.001 | 25.1 | 0.00 | | | Passes | No change |
| Aluminum | | | | | | | | | |
| 1 | 8.4489 | 8.4479 | 0.001 | 24.7 | 0.00 | 0.00 | <1 | Passes | No change |
| 2 | 7.7643 | 7.763 | 0.0013 | 24.7 | 0.00 | | | Passes | No change |
| Cast Iron | | | | | | | | | |
| 1 | 30.7591 | 30.7586 | 0.0005 | 28.3 | 0.00 | 0.00 | <1 | Passes | No change |
| 2 | 29.6531 | 29.652 | 0.0011 | 28.3 | 0.00 | | | Passes | No change |
| Brass | | | | | | | | | |
| 1 | 19.7642 | 19.7587 | 0.0055 | 34.8 | 0.02 | 0.03 | <2 | Passes | No change |
| 2 | 19.6996 | 19.6912 | 0.0084 | 34.8 | 0.03 | | | Passes | No change |
| Copper | | | | | | | | | |
| 1 | 26.7761 | 26.7712 | 0.0049 | 24.9 | 0.02 | 0.02 | <2 | Passes | No change |
| 2 | 26.8692 | 26.8621 | 0.0071 | 24.9 | 0.03 | | | Passes | No change | pH after test: 8.73

*Fig. 1*

Brake Fluid Corrosion test: Commercial Brake Fluid + 50 ppm copper added

Method: FMVSS-116, Para S6.6

| Metal | Initial Wt | Final Wt | Wt Change | Area (sq. cm.) | Wt Change (mg/sq.cm.) | Av. Wt Change (mg/sq.cm.) | Requirement (mg/sq.cm.) | Comments Wt Loss | Appearance |
|---|---|---|---|---|---|---|---|---|---|
| Tinned Iron | | | | | | | | | |
| 1 | 1.8247 | 1.8217 | 0.003 | 21.5 | 0.01 | 0.01 | <1 | Passes | sl. Pitting |
| 2 | 1.8687 | 1.8661 | 0.0026 | 21.5 | 0.01 | | | Passes | No change |
| Steel | | | | | | | | | |
| 1 | 20.4968 | 20.4935 | 0.0033 | 25.1 | 0.01 | 0.01 | <1 | Passes | No change |
| 2 | 20.4964 | 20.4941 | 0.0023 | 25.1 | 0.01 | | | Passes | No change |
| Aluminum | | | | | | | | | |
| 1 | 7.9181 | 7.9144 | 0.0017 | 24.7 | 0.01 | 0.01 | <1 | Passes | No change |
| 2 | 3.8387 | 3.8385 | 0.0002 | 24.7 | 0.01 | | | Passes | No change |
| Cast Iron | | | | | | | | | |
| 1 | 29.7345 | 29.7321 | 0.0024 | 26.3 | 0.01 | 0.01 | <1 | Passes | sl. Pitting |
| 2 | 26.7877 | 26.7834 | 0.0043 | 26.3 | 0.02 | | | Passes | sl. Pitting |
| Brass | | | | | | | | | |
| 1 | 21.4733 | 21.4720 | 0.0033 | 24.8 | 0.01 | 0.01 | <2 | Passes | No change |
| 2 | 16.9772 | 16.9751 | 0.0021 | 24.8 | 0.01 | | | Passes | No change |
| Copper | | | | | | | | | |
| 1 | 25.9231 | 25.9212 | 0.0019 | 24.9 | 0.01 | 0.01 | <2 | Passes | No change |
| 2 | 25.6558 | 25.6538 | 0.0032 | 24.9 | 0.01 | | | Passes | No change | pH after test: 6.91

*Fig. 2*

Brake Fluid Corrosion Test: Commercial Brake Fluid + 100 ppm copper added

Method: FMVSS-116, Para S6.6

| Metal | Initial Wt | Final Wt | Wt Change | Area (sq. cm.) | Wt Change (mg/sq.cm.) | Av. Wt Change (mg/sq.cm.) | Requirement (mg/sq.cm.) | Comments Wt Loss | Appearance |
|---|---|---|---|---|---|---|---|---|---|
| Tinned Iron | | | | | | | | | |
| 1 | 1.9395 | 1.9374 | 0.0021 | 21.5 | 0.01 | 0.01 | <.1 | Passes | sl. Pitting |
| 2 | 1.8381 | 1.8347 | 0.0034 | 21.5 | 0.01 | | | Passes | No change |
| Steel | | | | | | | | | |
| 1 | 22.5632 | 22.5589 | 0.0043 | 25.1 | 0.02 | 0.02 | <.1 | Passes | No change |
| 2 | 22.8593 | 22.8539 | 0.0052 | 25.1 | 0.01 | | | Passes | No change |
| Aluminum | | | | | | | | | |
| 1 | 3.8464 | 3.8443 | 0.0021 | 24.7 | 0.01 | 0.01 | <.1 | Passes | No change |
| 2 | 3.9333 | 3.9314 | 0.0017 | 24.7 | 0.01 | | | Passes | No change |
| Cast Iron | | | | | | | | | |
| 1 | 25.2947 | 25.2916 | 0.0031 | 26.3 | 0.01 | 0.01 | <.1 | Passes | sl. Pitting |
| 2 | 23.0506 | 23.0488 | 0.0036 | 26.3 | 0.01 | | | Passes | No change |
| Brass | | | | | | | | | |
| 1 | 22.7888 | 22.7851 | 0.0037 | 24.8 | 0.01 | 0.02 | <.2 | Passes | No change |
| 2 | 21.8033 | 21.7994 | 0.0039 | 24.8 | 0.02 | | | Passes | No change |
| Copper | | | | | | | | | |
| 1 | 10.3448 | 10.3422 | 0.0026 | 24.9 | 0.01 | 0.01 | <.2 | Passes | No change |
| 2 | 26.8127 | 26.8108 | 0.0019 | 24.9 | 0.01 | | | Passes | No change | pH after test: 6.54

*Fig. 3*

Brake Fluid Corrosion test: Commercial Brake Fluid + 200 ppm copper added

Method: FMVSS-116, Para S6.6

| Metal | Initial Wt | Final Wt | Wt Change | Area (sq. cm.) | Wt Change (mg/sq.cm.) | Av. Wt Change (mg/sq.cm.) | Requirement (mg/sq.cm.) | Comments Wt Loss | Appearance |
|---|---|---|---|---|---|---|---|---|---|
| Tinned Iron | | | | | | | | | |
| 1 | 1.9613 | 1.9595 | 0.0018 | 21.5 | 0.01 | 0.01 | <.1 | Passes | sl. Pitting |
| 2 | 1.9263 | 1.9238 | 0.0025 | 21.5 | 0.01 | | | Passes | sl. Pitting |
| Steel | | | | | | | | | |
| 1 | 22.5128 | 22.5087 | 0.0041 | 25.1 | 0.02 | 0.02 | <.1 | Passes | Pitted + Rust |
| 2 | 19.5634 | 19.5575 | 0.0059 | 25.1 | 0.02 | | | Passes | Pitted + Rust |
| Aluminum | | | | | | | | | |
| 1 | 3.5737 | 3.5714 | 0.0023 | 24.7 | 0.01 | 0.01 | <.1 | Passes | sl. Pitting |
| 2 | 7.1000 | 7.0992 | 0.0008 | 24.7 | 0.00 | | | Passes | No change |
| Cast Iron | | | | | | | | | |
| 1 | 29.3623 | 29.3464 | 0.016 | 26.3 | 0.06 | 0.06 | <.1 | Passes | Pitted + Rust |
| 2 | 26.8823 | 26.8698 | 0.0125 | 26.3 | 0.05 | | | Passes | Pitted + Rust |
| Brass | | | | | | | | | |
| 1 | 22.9237 | 22.9222 | 0.0015 | 24.8 | 0.01 | 0.01 | <.2 | Passes | No change |
| 2 | 21.9813 | 21.9789 | 0.0024 | 24.8 | 0.01 | | | Passes | No change |
| Copper | | | | | | | | | |
| 1 | 25.343 | 25.3411 | 0.0019 | 24.9 | 0.01 | 0.01 | <.2 | Passes | No change |
| 2 | 26.8048 | 26.8021 | 0.0027 | 24.9 | 0.01 | | | Passes | No change | pH after test: 5.36

*Fig. 4*

Commercial Brake Fluid Corrosion test: 200 ppm copper + 3.5% Water

| Metal | | Initial Wt | Final Wt | Wt Change | Area (sq. cm.) | Wt Change (mg/sq.cm.) | Av. Wt Change (mg./sq.cm.) | Requirement (mg./sq.cm.) | Comments | |
|---|---|---|---|---|---|---|---|---|---|---|
| | | | | | | | | | Wt. loss | Appearance |
| Tinned Iron | | | | | | | | | | |
| | 1 | 1.8766 | 1.8758 | 0.0008 | 21.3 | 0.00 | 0.00 | <1 | Passes | No change |
| | 2 | 1.9866 | 1.9859 | 0.0007 | 21.3 | 0.00 | | | Passes | No change |
| Steel | | | | | | | | | | |
| | 1 | 21.3382 | 21.3282 | 0.0100 | 25.1 | 0.04 | 0.04 | <1 | Passes | Pitting + Rust |
| | 2 | 20.6673 | 20.6582 | 0.0091 | 25.1 | 0.03 | | | Passes | Pitting + Rust |
| Aluminum | | | | | | | | | | |
| | 1 | 5.4332 | 5.4323 | 0.0009 | 24.7 | 0.00 | 0.00 | <1 | Passes | sl. Pitting |
| | 2 | 6.7741 | 6.7732 | 0.0009 | 24.7 | 0.00 | | | Passes | Pitting |
| Cast Iron | | | | | | | | | | |
| | 1 | 30.8881 | 30.8798 | 0.0083 | 26.3 | 0.03 | 0.04 | <1 | Passes | Pitting + Rust |
| | 2 | 30.7998 | 30.7865 | 0.0133 | 26.3 | 0.05 | | | Passes | Pitting + Rust |
| Brass | | | | | | | | | | |
| | 1 | 21.7645 | 21.7601 | 0.0044 | 24.8 | 0.02 | 0.02 | <2 | Passes | No change |
| | 2 | 22.6751 | 22.6712 | 0.0039 | 24.8 | 0.02 | | | Passes | No change |
| Copper | | | | | | | | | | |
| | 1 | 27.8865 | 27.8789 | 0.0076 | 24.9 | 0.03 | 0.03 | <2 | Passes | No change |
| | 2 | 27.8871 | 27.8793 | 0.0078 | 24.9 | 0.03 | | | Passes | No change | pH 5.48 after test

*Fig. 5*

Brake Fluid Corrosion test: 200 ppm copper, used brake fluid, client supplied

| Metal | | Initial Wt | Final Wt | Wt Change | Area (sq. cm.) | Wt Change (mg/sq.cm.) | Av. Wt Change (mg./sq.cm.) | Requirement (mg./sq.cm.) | Comments | |
|---|---|---|---|---|---|---|---|---|---|---|
| | | | | | | | | | Wt. loss | Appearance |
| Tinned Iron | | | | | | | | | | |
| | 1 | 1.9387 | 1.9380 | 0.0007 | 21.3 | 0.03 | 0.00 | <1 | Passes | No change |
| | 2 | 1.9567 | 1.9562 | 0.0005 | 21.3 | 0.03 | | | Passes | No change |
| Steel | | | | | | | | | | |
| | 1 | 19.7512 | 19.7492 | 0.002 | 25.1 | 0.01 | 0.03 | <1 | Passes | Pitting + Rust |
| | 2 | 19.6673 | 19.6521 | 0.0152 | 25.1 | 0.06 | | | Passes | Pitting + Rust |
| Aluminum | | | | | | | | | | |
| | 1 | 3.8228 | 3.8226 | 0.0002 | 24.7 | 0.00 | 0.00 | <1 | Passes | sl. Pitting |
| | 2 | 3.7889 | 3.7885 | 0.0004 | 24.7 | 0.00 | | | Passes | No change |
| Cast Iron | | | | | | | | | | |
| | 1 | 29.7277 | 29.705 | 0.0227 | 26.3 | 0.09 | 0.10 | <1 | Passes | Pitting + Rust |
| | 2 | 29.7484 | 29.7194 | 0.0290 | 26.3 | 0.11 | | | Passes | Pitting + Rust |
| Brass | | | | | | | | | | |
| | 1 | 23.032 | 23.0261 | 0.0059 | 24.8 | 0.02 | 0.03 | <2 | Passes | No change |
| | 2 | 22.7782 | 22.7709 | 0.0073 | 24.8 | 0.03 | | | Passes | No change |
| Copper | | | | | | | | | | |
| | 1 | 26.1329 | 26.1287 | 0.0062 | 24.9 | 0.03 | 0.04 | <2 | Passes | No change |
| | 2 | 27.4332 | 27.4201 | 0.0131 | 24.9 | 0.05 | | | Passes | No change | pH 5.24 after test

*Fig. 6*

CORROSION INHIBITING HYDRAULIC FLUID ADDITIVE

CROSS-REFERENCE TO RELATED APPLICATIONS

The present application claims the benefit of U.S. Provisional Patent Application Ser. No. 61/944,530, filed Feb. 25, 2014 and entitled CORROSION INHIBITING HYDRAULIC FLUID ADDITIVE, which is incorporated by reference as though set forth herein in its entirety.

The present application is also related to:

U.S. Pat. No. 6,651,487, entitled TEST FOR BRAKE FLUID AGE AND CONDITION, which issued on Nov. 25, 2003;

U.S. Pat. No. 6,691,562, entitled TEST FOR BRAKE FLUID AGE AND CONDITION, which issued on Feb. 17, 2004;

U.S. Pat. No. 7,152,636, entitled BRAKE FLUSH ACCELERATOR, which issued on Dec. 26, 2006;

U.S. Pat. No. 7,682,834, entitled COLORIMETRIC TEST FOR BRAKE FLUID, which issued on Mar. 23, 2010;

U.S. Pat. No. 8,021,890, entitled COLORIMETRIC TEST FOR BRAKE SYSTEM CORROSION, which issued on Sep. 20, 2011; and U.S. Pat. No. 8,216,849, entitled COLORIMETRIC TEST FOR BRAKE SYSTEM CORROSION, which issued on Jul. 10, 2012.

The foregoing documents are incorporated by reference as though set forth herein in their entirety.

TECHNICAL FIELD

The technology disclosed herein relates to hydraulic fluid. More specifically, this disclosure relates to additives for enhancing the properties of hydraulic fluids, such as inhibition of corrosion of brake fluid.

BACKGROUND

Brake fluid is used to transmit the pressure exerted on a motor vehicle's brake pedal to the slave cylinders of the braking system. The most commonly used brake fluids in North America consist of glycol-based liquids categorized as DOT3 and DOT4 on the basis of the boiling point resulting from their particular composition. In order to prevent boiling of the fluid caused by overheating during use, DOT3 and DOT4 fluids are required to have a dry boiling point (with no moisture in fluid) of at least 401° F. (205° C.) and 446° F. (230° C.), respectively, so that proper brake operation is ensured under all temperature conditions.

All types of glycol-based brake fluid are hygroscopic. As a result of this property, they readily absorb moisture that reduces their boiling point.

Another important aspect of brake systems maintenance is the corrosive nature of some of their constituents, which, upon contamination of the brake fluid, progressively contribute to damage metallic tubing and other parts of the brake system. Most brake lines consist of steel lined with a copper alloy. Brake lines typically represent the largest surface area of metal in contact with brake fluid. A typical light-duty vehicle uses about 14 meters of such copper-lined steel tubing with an inside diameter of about 2.5 mm, for a total internal surface area of about 1,200 $cm^2$. Therefore, corrosion of these lines contributes relatively large amounts of copper ions to the fluid. The master and slave cylinders and antilock brake system (ABS) include components made of steel, aluminum, zinc, or other materials that are also susceptible to corrosion as the fluid ages, its water content increases and its reserve alkalinity decreases. Dissolved iron is also known to appear in brake fluid after the initial amine corrosion inhibitor is significantly depleted and the dissolved copper level reaches about 200 ppm. By the time this event occurs, the brake fluid is highly corrosive and damaging to the brake system, and its replacement is called for regardless of its actual service time or mileage.

Corrosion inhibitors in new brake fluid inhibit corrosion initially. In conventional brake fluids, amines are included in the new brake fluid to inhibit corrosion and prevent damage to metal parts that operate in contact with the fluid. Corrosion inhibitors deplete with time, temperature, and environmental stress (for example, air, moisture, salts, ions, and other contaminants seeping into the fluid). As the corrosion inhibitors deplete, corrosion accelerates. As the brake fluid ages, its anticorrosive properties are measured in terms of reserve alkalinity; that is, the amount of amines remaining in the fluid to buffer the acidity resulting from breakdown of fluid constituents. Over time, thermal oxidation and volatization produce a significant reduction of the amine content and the concurrent decrease of anticorrosive properties. Tests have shown that the reserve alkalinity of DOT3 and DOT4 fluids is reduced to about 20 percent of its original value after 18 to 20 months of normal operation.

Corrosion in the brake system is harmful, and at some point internal corrosion may interfere with the proper operation of the brakes or antilock brake system (ABS). Copper deposition onto brake system components, particularly ABS seats and valves, is also undesirable and may interfere with the proper operation of the brakes or ABS. A finite level of copper ions in brake fluid with water will cause corrosion of ferrous metals like iron, cast iron, steel, and the like in the brake system. The level of copper ions in brake fluid with water (as low as 2% water) is an indicator of the virtual age of the brake fluid and the potential for corrosion of ferrous metals.

Copper is of interest in brake system corrosion because copper can form stable ions in water-free (dry) inhibited commercial brake fluid, and thus copper can begin corroding immediately upon contact with brake fluid in the presence of oxygen. Copper is also an oxidizer for other metals. Iron ions, on the other hand, have limited solubility in dry commercial brake fluid. Iron begins to corrode when brake fluid takes on water and/or the corrosion inhibitors become depleted. Iron may be oxidized by oxygen, water, and copper ions in the brake fluid. Copper oxidizes iron in the same manner as oxygen, with a copper ion gaining an electron from an iron atom, plating or depositing a copper atom on or near the iron substrate, and releasing an iron ion into solution. The copper level in brake fluid is directly proportional to the corrosivity of the brake fluid, or its potential corrosivity.

However, copper is not the only species of interest in brake system corrosion. Iron, zinc, tin, aluminum, and brass (an alloy of copper and zinc) are also found in brake systems, and these materials are susceptible to corrosion. Any of these materials, or their ions, may be referred to as a reactive constituent of brake fluid because of their susceptibility to corrosion.

Therefore, brake fluids also need to be checked and periodically replaced in order to prevent dangerous corrosion in the brake system. Accordingly, industry maintenance recommendations, where such exist, are typically based on service time and mileage of the vehicle.

U.S. Pat. No. 6,691,562 discloses an approach for estimating service time and/or mileage of brake fluid based on the recognition that the copper content in brake fluid is predictably related to time and mileage of vehicle operation. Thus, this correlation can be advantageously used to estimate milestones for maintenance purposes without regard to actual service time and/or mileage. Instead, copper content is adopted as a reliable indicator of a brake system's or a vehicle's "virtual age," a term used to refer to the wear and tear on brake fluid resulting from actual mileage, actual service conditions, and/or time of service.

SUMMARY

The various aspects of the disclosed technology have been developed in response to the present state of the art, and in particular, in response to the problems and needs in the art that have not yet been fully solved by currently available hydraulic fluids, hydraulic fluid additives, or hydraulic fluid maintenance practices. The systems and methods disclosed herein may inhibit corrosion of hydraulic system components in the presence of an existing (used) hydraulic fluid, without the need to exchange the entire volume of hydraulic fluid in the system.

The present disclosure is related in general to methods and substances for boosting corrosion inhibition in a brake system based on the recognition that the copper content in brake fluid is predictably related to corrosion of brake system materials, such as ferrous metals like iron and its alloys, and deposition of metallic copper in the vicinity of corroding brake system materials. In particular, the present disclosure pertains to corrosion inhibiting brake fluid additives and methods of use, by which the anticorrosive properties of used brake fluid may be restored before the brake fluid reaches the point of replacement. In some methods of use, a corrosion inhibiting brake fluid additive may be added to the existing brake fluid in a brake system. In other methods of use, existing brake fluid in a brake system may first be tested to determine the current content of one or more reactive constituents in the brake fluid, and, if the current content of the reactive constituent(s) is within a predetermined range of values, a corrosion inhibiting brake fluid additive may then be added to the brake fluid to inhibit further corrosion of brake system components. The reactive constituents may be metals such as copper, iron, zinc, tin, or aluminum, among others.

In an aspect of the technology, a method of testing a hydraulic fluid in a hydraulic system includes the steps of: testing a sample of a hydraulic fluid, wherein the hydraulic fluid is in a hydraulic system; evaluating at least one test result to quantify a concentration of a metal of interest in the hydraulic fluid; and based on the concentration of the metal of interest in the hydraulic fluid, determining whether a corrosion inhibiting hydraulic fluid additive should be added to the hydraulic fluid.

Embodiments of this aspect of the technology may include one or more of the following features. The hydraulic fluid may be brake fluid and the hydraulic system may be a brake system of a vehicle. The metal of interest may be selected from the group consisting of copper, iron, zinc, tin, and aluminum. The metal of interest may be copper. Determining whether the corrosion inhibiting hydraulic fluid additive should be added to the hydraulic fluid may include determining that the corrosion inhibiting hydraulic fluid additive should be added if the concentration of copper is greater than 50 parts per million. Testing the sample of hydraulic fluid may include exposing a reactive strip to the sample; and wherein evaluating at least one test result may include comparing the reactive strip to a color standard representing a correlation between color and concentration the metal of interest in the sample. Determining whether the corrosion inhibiting hydraulic fluid additive should be added to the hydraulic fluid may include determining that the corrosion inhibiting hydraulic fluid additive should be added to the hydraulic fluid, the method further including, in response to determining that the corrosion inhibiting hydraulic fluid additive should be added to the hydraulic fluid, adding the corrosion inhibiting hydraulic fluid additive to the hydraulic fluid. Determining whether the corrosion inhibiting hydraulic fluid additive should be added to the hydraulic fluid may include determining that the hydraulic fluid requires replacement, the method further including, in response to determining that the hydraulic fluid requires replacement: removing the hydraulic fluid from the hydraulic system; and inserting a quantity of new hydraulic fluid into the hydraulic system. Determining whether the corrosion inhibiting hydraulic fluid additive should be added to the hydraulic fluid may include determining that the corrosion inhibiting hydraulic fluid additive is not needed by the hydraulic fluid, the method further including, in response to determining that the corrosion inhibiting hydraulic fluid additive is not needed by the hydraulic fluid, preparing the hydraulic system for further operation without the corrosion inhibiting hydraulic fluid additive. The corrosion inhibiting brake fluid additive may be benzotriazole.

In another aspect of the technology, a method of treating hydraulic fluid of a hydraulic system may include the steps of: opening the hydraulic system to obtain access to the hydraulic fluid; adding a hydraulic fluid additive to the hydraulic fluid; closing the hydraulic system to capture the hydraulic fluid and the additive; and in response to addition of the additive to the hydraulic fluid, inhibiting corrosion of the hydraulic system.

Embodiments of this aspect of the technology may include one or more of the following features. The hydraulic fluid additive may include a copper corrosion inhibitor. The copper corrosion inhibitor may be an organic compound. The organic compound may be an azole. The azole may be benzotriazole. After adding the hydraulic fluid additive to the hydraulic fluid, a mixture of the hydraulic fluid additive and the hydraulic fluid may include 0.01% to 0.2% benzotriazole by weight. The hydraulic fluid additive may be provided in a volume of about 1 fluid ounce, with 0.45% benzotriazole by weight. The hydraulic fluid additive may be provided in a volume of about 3 ounces, with 0.15% benzotriazole by weight. The method may include the step of measuring the concentration of copper in the hydraulic fluid before adding the hydraulic fluid additive to the hydraulic fluid. The measured concentration of copper in the hydraulic fluid may be less than 200 ppm copper. The concentration of copper in the hydraulic fluid may be less than 150 ppm copper. The concentration of copper in the hydraulic fluid may be less than 100 ppm copper. The concentration of copper in the hydraulic fluid may be less than 50 ppm copper. Measuring the concentration of copper in the hydraulic fluid may include the steps of: exposing a copper reactive strip to the hydraulic fluid for reaction with copper in the hydraulic fluid; and comparing a color resulting on the exposed copper reactive strip to a color standard representing a correlation between color and concentration of copper.

In yet another aspect of the technology, a corrosion inhibiting hydraulic fluid additive may include: benzotriazole; and a carrier fluid; wherein the carrier fluid has a composition selected such that post-additive operating characteristics of a hydraulic system after addition of the hydraulic fluid additive to hydraulic fluid in the hydraulic system, are substantially equivalent to pre-additive operating characteristics of the hydraulic system prior to addition of the hydraulic fluid additive.

Embodiments of this aspect of the technology may include one or more of the following features. The carrier fluid may be a glycol. The benzotriazole may be between 0.005% by weight and 1.0% by weight of the hydraulic fluid additive. The benzotriazole may be between 0.010% by weight and 0.75% by weight of the hydraulic fluid additive. The benzotriazole may be between 0.15% by weight and 0.45% by weight of the hydraulic fluid additive. The corrosion inhibiting hydraulic fluid additive may include: an ingredient selected from the group consisting of corrosion inhibitors for non-cuprous metals, oxygen scavengers, antioxidants, sulfur scavengers, buffers, catalysts, stabilizers, detergents, emulsifiers, carriers, fillers, glycol ethers, azoles, salts, acids, bases, and amines.

In yet another aspect of the technology, a kit may include: a container of a brake fluid additive formulated to inhibit corrosion of a brake system in response to addition of the brake fluid additive to brake fluid within the brake system; and at least one brake fluid test strip that, in response to exposure to the brake fluid, indicates a concentration of a metal of interest within the brake fluid; wherein the metal of interest is a product of corrosion of the brake system.

Embodiments of this aspect of the technology may include one or more of the following features. The metal of interest may be selected from the group consisting of copper, iron, zinc, tin, and aluminum. The metal of interest may be copper. The at least one brake fluid test strip may be carried by the container. The kit may include: a color standard representing a correlation between metal ion content in a brake fluid sample and brake fluid test strip color after reaction with the species of metal ions. The color standard may be carried by the container.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the technology's scope, the exemplary embodiments of the technology will be described with additional specificity and detail through use of the accompanying drawings in which:

FIG. 1 is a table containing data from a United States Federal Motor Vehicle Safety Standard 116 corrosion test (FMVSS-116 S5.1.6) of commercial brake fluid with 5% water and 0 parts per million (ppm) of copper;

FIG. 2 is a table containing data from a FMVSS-116 S5.1.6 corrosion test of commercial brake fluid with 5% water and 50 ppm of copper;

FIG. 3 is a table containing data from a FMVSS-116 S5.1.6 corrosion test of commercial brake fluid with 5% water and 100 ppm of copper;

FIG. 4 is a table containing data from a FMVSS-116 S5.1.6 corrosion test of commercial brake fluid with 5% water and 200 ppm of copper;

FIG. 5 is a table containing data from a FMVSS-116 S5.1.6 corrosion test of commercial brake fluid with 2% water and 200 ppm of copper;

FIG. 6 is a table containing data from a FMVSS-116 S5.1.6 corrosion test of used commercial brake fluid with water and about 300 ppm of copper;

DETAILED DESCRIPTION

Figure 7:
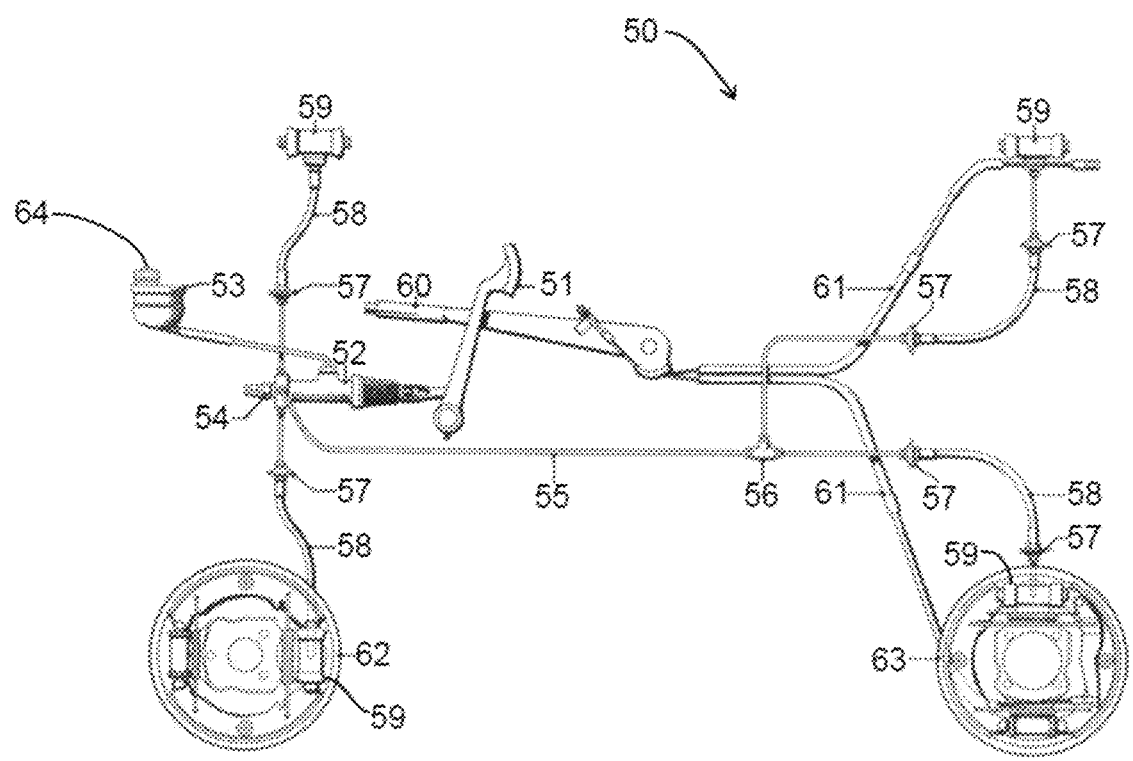
FIG. 7 is a diagram of a brake system.

Exemplary embodiments of the technology will be best understood by reference to the drawings, wherein like parts are designated by like numerals throughout. It will be readily understood that the components of the technology, as generally described and illustrated in the figures herein, could be combined, arranged and designed in a wide variety of different configurations. Thus, the following more detailed description of the embodiments of the apparatus, system, and method is not intended to limit the scope of the invention, as claimed.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

FIGS. 1-4 show tabulated data from United States Federal Motor Vehicle Safety Standard 116 corrosion tests (FMVSS-116 S5.1.6) of commercial brake fluid with 5% water and various levels of copper. The commercial brake fluid included a typical corrosion inhibitor package. The tests evaluated weight loss, pitting, and rusting of tinned iron, cast iron, steel, aluminum, brass, and copper after exposure to the test fluid for 5 days at 212° F. These tests were conducted to determine a copper threshold for brake system material corrosion.

FIG. 1 shows data for commercial brake fluid 0 ppm copper. FIG. 1 indicates that this brake fluid meets all of the requirements of FMVSS-116 S5.1.6. This data may be referred to as a baseline for comparison with the data in FIGS. 2-4, since this brake fluid includes no copper.

FIG. 2 shows data for commercial brake fluid with 50 ppm copper. FIG. 3 shows data for commercial brake fluid with 100 ppm copper. FIG. 4 shows data for commercial brake fluid with 200 ppm copper.

FIGS. 2-4 indicate that as the copper level increases, weight loss and pitting increases for steel and cast iron, and pH of the test solution decreases (the fluid becomes more acidic and more corrosive). While all of the metals tested pass the requirements for weight loss, steel, cast iron, tinned iron, and aluminum failed the requirements for surface pitting and rusting at 200 ppm copper (FIG. 4). Weight loss in steel, cast iron, and tinned iron due to corrosion may have been offset, or masked, by weight gain from copper deposition, or plating, on the metal samples.

FIG. 5 shows tabulated data from FMVSS-116 S5.1.6 corrosion tests of brake fluid with 2% water and 200 ppm copper. The tests evaluated weight loss, pitting, and rusting of tinned iron, cast iron, steel, aluminum, brass, and copper after exposure to the test fluid for 5 days at 212° F. This sample had results similar to those shown in FIG. 4, indicating that 2% water is sufficient for corrosion to occur in the presence of 200 ppm copper in brake fluid.

Based on the results in FIGS. 1-5, 200 ppm copper may be a triggering threshold for brake system material corrosion in brake fluid with 2% or more water. This copper level overwhelmed the corrosion inhibitor package in the commercial brake fluid.

FIG. 6 shows tabulated data from a FMVSS-116 S5.1.6 corrosion test of used brake fluid with about 300 ppm of copper. The used brake fluid was tested and found to have 292 ppm of copper. The test evaluated weight loss, pitting, and rusting of tinned iron, cast iron, steel, aluminum, brass, and copper after exposure to the test fluid for 5 days at 212° F. FIG. 6 shows data for used brake fluid with water and 292 ppm copper. This sample failed the requirements for surface pitting and rusting, indicating that the used brake fluid is due for replacement.

From these examples, it can be seen that an increase in copper content in brake fluid can result in degradation of the brake fluid to an extent that replacement will be required. The present invention may provide systems and methods whereby the corrosion inhibiting properties of brake fluid can be restored before the copper content of the brake fluid reaches unsafe levels. For example, the brake fluid may be tested for copper and, if the copper content is sufficient to warrant remediation, but not sufficient to require replacement of the brake fluid, the brake fluid may be amended through the use of a corrosion resisting additive, as will be set forth in detail below.

In some embodiments, the corrosion inhibiting brake fluid additive of the present disclosure may be used in connection with various brake fluid types, including but not limited to DOT 3, DOT 4, and DOT 5.1 brake fluid. The brake fluid additive may help these brake fluids pass applicable standards and/or tests, such as Federal Motor Vehicle Safety (FMVSS) standard 116, Society of Automotive Engineers (SAE) J1703 and J1704, and the like. The brake fluid additive may help the brake fluid satisfy tests for concentration of a metal of interest (such as copper) in the brake fluid after a period of use, tests for brake fluid appearance related to visible impurities, tests for brake fluid pH levels, and/or the like. The brake fluid additive may advantageously meet any applicable specifications for its effect on rubber, fluidity/appearance, and/or water tolerance. Advantageously, the brake fluid additive may still meet such applicable specifications, even when added to a brake system in a concentration much higher than recommended.

In some embodiments, the brake fluid additive of the present disclosure may provide a substantially immediate enhancement to the appearance of the brake fluid, which may be observable as soon as the brake fluid additive is mixed into the brake fluid. When added to a brake system with used brake fluid, the brake fluid additive may disperse throughout the brake system, for example, within about one week in an ABS-equipped vehicle, and within about three weeks in a non-ABS-equipped vehicle.

Further, in some embodiments, the brake fluid additive may raise the pH of some brake fluid types (such as DOT 3 brake fluid) and/or may leave the pH of some brake fluid types (such as DOT 4 brake fluid) substantially unchanged. For example, the brake fluid additive may raise the pH of DOT 3 brake fluid by approximately one, two, three, or four points. By way of further example, the brake fluid additive may keep the pH of DOT 4 brake fluid within approximately one-half point, one point, one-and-a-half points, or two points of the pH measurement prior to addition of the brake fluid. This may advantageously be accomplished with a single formulation so that the same brake fluid additive may be added to either DOT 3 or DOT 4, or even DOT 5.1 brake fluid.

Referring to FIG. 7, a simple brake system 50 includes a brake pedal 51, a master cylinder 52, a brake fluid reservoir 53, a brake fluid reservoir cap 64, a brake light switch 54, rigid brake lines 55, a three way connector 56, brackets 57, flexible brake hoses 58, wheel cylinders 59, a hand brake lever 60, cable guide tubes 61, a front brake 62, and a rear brake 63. A second front brake and second rear brake are omitted from FIG. 7 in the interest of clarity. The simple brake system 50 is shown only by way of example; the present invention may be used with many types of hydraulic systems, including but not limited to brake systems of all types including those with ABS, other vehicular fluids such as transmission fluid, engine oil, power steering fluid, and other hydraulic fluids such as those used in industrial machinery. Thus, although the following description references a corrosion inhibiting brake fluid additive, the principles of the present invention may be used to provide additives and/or associated methods for a wide variety of fluids.

In used brake fluids, particularly those with less than 200 ppm copper, a corrosion inhibiting brake fluid additive with a concentrate of benzotriazole (BZT; also known as BTA) may restore at least some of the anticorrosive properties of the used brake fluid, particularly the copper corrosion resistance. For example, the corrosion inhibiting brake fluid additive may contain sufficient BZT to provide 0.005% to 0.75%, 0.005% to 0.475%, 0.005% to 0.35%, 0.005% to 0.275%, 0.01% to 0.02%, 0.01% to 0.2%, or 0.1% to 0.2% BZT by weight when mixed with used brake fluid in a brake system. The mixture of corrosion inhibiting brake fluid additive and used brake fluid may inhibit further corrosion of metallic brake system components. The concentration of BZT in the mixture may be adjusted up or down among or beyond these stated values to provide sufficient copper corrosion resistance for the internal surface area of copper in a specific brake system, while avoiding precipitation.

The corrosion inhibiting brake fluid additive may be formulated as a small fraction of the total volume of the intended brake system. For example, in a passenger car or other typical light-duty vehicle, the brake system may contain approximately one liter of brake fluid, such as 0.9 to 1.1 liters of brake fluid. In this case, the volume of corrosion inhibiting brake fluid additive may be between about 30 milliliters and about 90 milliliters (1 to 3 fluid ounces), 15 to 240 milliliters (0.5 to 8 fluid ounces), 20 to 150 milliliters (0.65 to 5 fluid ounces), 25 to 120 milliliters (0.8 to 4 fluid ounces). The corrosion inhibiting brake fluid additive may be up to 25% of the brake system volume, and may contain 0.15% to 0.45% BZT by weight. In one example, the volume of corrosion inhibiting brake fluid additive is 30 milliliters (1 fluid ounce), with 0.45% BZT by weight. In another example, the volume of corrosion inhibiting brake fluid additive is 90 milliliters (3 fluid ounces), with 0.15% BZT by weight. The volume of brake fluid in brake systems for other vehicles may be less than or greater than one liter. Other vehicles may include motorcycles, all-terrain vehicles, limousines and other stretched vehicles, buses, trucks, or military vehicles, among others. Brake system fluid capacity, or volume, may be less than 10 milliliters, 10 to 100 milliliters, 100 to 1000 milliliters, or 1 to 3 liters, and the weight percent BZT in the corrosion inhibiting brake fluid additive and the total volume of additive may be adjusted proportionately to the brake system volume and the internal surface area of each corrodible or reactive material in the brake system. Multiple formulations of corrosion inhibiting brake fluid additive may be provided. The different formulations may be customized for different brake systems, different fluid capacities, different service conditions, or for brake fluids with different virtual ages or metal ion contents.

BZT is one example of a copper corrosion inhibitor which may be included in the corrosion inhibiting brake fluid additive. Copper corrosion inhibitors may include organic compounds and inorganic compounds. Organic copper corrosion inhibitors may include, but are not limited to, azoles (including BZT), azole derivatives such as CUVAN®, marketed by Vanderbilt Chemicals LLC, amines, amino acids, triphenylmethane derivatives, thiole group compounds, phosphates, potassium ethyl xanthate, sodium dodecylsulfate (SDS), phthalazin derivatives, gamma-pyrodiphenone, tannins, substituted uracils, propargyl alcohol, aniline derivatives, phthalimides, purine, caffeine, and isatin. Organic copper corrosion inhibitors may include heteroatoms such as nitrogen, sulfur, or phosphorus. Inorganic copper corrosion inhibitors may include, but are not limited to, chromate $CrO_4^{2-}$, molybdate $MoO_4^{2-}$, and tetraborate $B_4O_7^{2-}$.

In alternative embodiments of the invention, a corrosion inhibiting brake fluid additive may include any of a wide variety of inhibitors besides BZT, including but not limited to any of those listed above. Additionally or alternatively, the present invention may include multiple corrosion inhibitors in various relative concentrations.

Additionally or alternatively, an additive according to the present invention may include inhibitors for corrosion besides copper corrosion. For example, iron, zinc, tin, aluminum, and/or brass corrosion inhibitors, or inhibitors for corrosion of other materials, may be used. The corrosion inhibiting brake fluid additive may contain other ingredients, such as corrosion or rust inhibitors for non-cuprous metals, oxygen scavengers, antioxidants, sulfur scavengers, buffers, catalysts, stabilizers, detergents, emulsifiers, carriers, fillers, glycol ethers, azoles, salts, acids, bases, amines, and the like.

While the preceding description has been made in the context of corrosion inhibiting additives for brake fluid, these principles, concepts, and examples may apply to other vehicle fluid systems or to other hydraulic systems.

Figure 8:
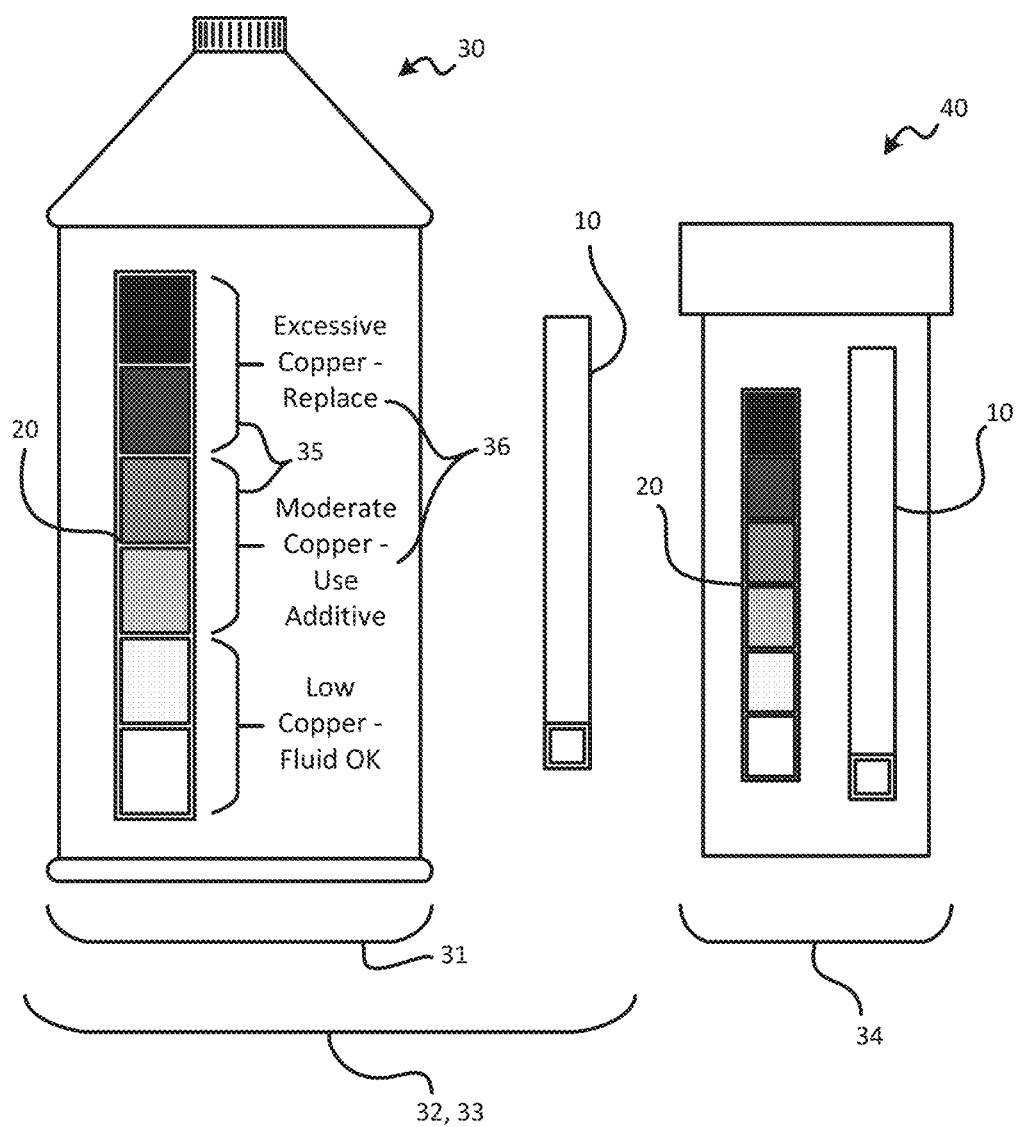
FIG. 8 is a side view of a container of corrosion inhibiting brake fluid additive, a brake fluid test strip, and a container of brake fluid test strips.

FIG. 8 is a side view of a container 30 of corrosion inhibiting brake fluid additive, a brake fluid test strip 10, and a second container 40 of brake fluid test strips 10. The container 30 may hold 1 to 3 ounces of the corrosion inhibiting brake fluid additive, or a different volume which is smaller than 1 ounce or larger than 3 ounces. The volume of container 30 is determined by the volume of corrosion inhibiting brake fluid additive, and different container sizes may be provided for different brake systems.

The container 30 may carry a color chart 20, as FIG. 8 shows. This arrangement may be referred to as a kit 31 which includes a container 30 of corrosion inhibiting brake fluid additive and a color standard, which may take the form of the color chart 20. The color chart 20 is shown carried on an exterior surface of the container 30, but in other examples, the color chart, if present, may be carried externally, internally, or covered by a removable label, overwrap, or membrane. The color chart 20 may also be provided on a packaging element associated with the container 30, such as a backing card of a blister package or a box enclosing the container 30. The color chart 20 may include several color swatches, each swatch corresponding to the color of a brake fluid test strip after reaction with a known concentration of a species of metal ions in a brake fluid sample.

A brake fluid test strip 10 is shown with the container 30; more than one brake fluid test strip 10 may optionally be present. For example, 2, 3, 4, or more brake fluid test strips 10 may be present. This arrangement may be referred to as a kit 32 which includes a container 30 of corrosion inhibiting brake fluid additive, a color standard, which may take the form of a color chart 20, and at least one brake fluid test strip 10. The kit 32 may include an alternative container, which may be the same as the container 30, which carries both the brake fluid test strip 10 and the color chart 20. The kit 32 may be packaged as described below. Yet another version of the container 30 may carry only the brake fluid test strips 10, without the color chart 20. This arrangement may be referred to as a kit 33 which includes a container 30 of corrosion inhibiting brake fluid additive and at least one brake fluid test strip 10.

The brake fluid test strips 10 and/or color chart 20 may be separate from the container 30. If separate, the brake fluid test strips 10 and/or color chart 20 may be packaged with the container 30 as a kit 32, for example in a single- or multi-compartment blister package or clamshell package (packages are not shown). FIG. 8 also shows that the brake fluid test strips 10 may be packaged in a second container 40, which may be provided separately from the container 30. One, two, three, four, or more brake fluid test strips 10 may be in the second container 40. The second container 40 may carry a color chart 20, as FIG. 8 shows. This arrangement may be referred to as a kit 34 which includes at least one brake fluid test strip 10 and a color standard, which may optionally take the form of a color chart 20. The kit 34 may or may not include the second container 40.

The color chart 20 is shown carried on an exterior surface of the second container 40 in FIG. 8, but in other examples, the color chart, if present, may be carried externally, internally, or covered by a removable label, overwrap, or membrane. The color chart 20 may also be provided on a packaging element associated with the brake fluid test strips, such as a backing card of a blister package or a box enclosing the brake fluid test strip 10 or the second container 40. Another color standard may be provided instead of the color chart 20. For example, the color standard may be provided as an application for an electronic device such as a smartphone, tablet, laptop, or the like. The application may display colors for comparison with a test strip 10 which has been exposed to brake fluid, and may make use of an onboard camera to acquire an image of the exposed test strip for analysis by the application.

A user may procure the container 30 of corrosion inhibiting brake fluid additive, the color standard or color chart 20, and the brake fluid test strip(s) 10 separately and assemble them for use as kit 32. In one example of this arrangement, a user may obtain the container 30 of corrosion inhibiting brake fluid additive and, separately, the kit 34 with at least one brake fluid test strip 10 and a color standard. The user may obtain the kit 34 first, test the brake fluid in a vehicle(s), determine how many containers 30 of corrosion inhibiting brake fluid additive are needed based on the test result(s), obtain the containers 30, and add the corrosion inhibiting brake fluid additive to those brake systems that need the additive.

The corrosion inhibiting brake fluid additive, brake fluid test strip 10, color chart 20 or other color standard, containers 30, 40, and/or kits 32, 33, 34 may be packaged in bulk for frequent users, such as automotive repair shops. In one example, several containers 30 of corrosion inhibiting brake fluid additive may be packaged together in a carton or case. For example, 12 containers 30 may be packaged together in a 4×3 array in a rectangular carton sized to receive the containers 30 with clearance. In another example, 11 containers 30 may be packaged together in the carton or case, with a second container 40 of brake fluid test strips 10 occupying the twelfth position. Other quantities of containers 30 may be provided in a case or a carton; preferred quantities may produce an orderly rectilinear array of containers 30 in the carton or case. The second container 40, if provided, may occupy a position in the array, and may include a number of brake fluid test strips 10. The number of brake fluid test strips 10 in the second container 40 may be 1, 2, 3, 4, or more times the number of containers 30 of the corrosion inhibiting brake fluid additive in the case or carton. This arrangement provides a frequent user with enough test strips 10 to test several brake systems per container 30 that is used.

The container 30 of corrosion inhibiting brake fluid additive may be packaged with a container of brake fluid. For example, the container 30 and the container of brake fluid may be joined by a neck hanger or neck coupler that encircles the container necks and extends between them, by an overwrap or shrink-wrap, by a sleeve, or by an outer box. Kit 32, 33, 34 may also be packaged with the container of brake fluid in similar fashion.

The brake fluid test strips and/or color chart may include instructions or indicia. These instructions or indicia may address use of the corrosion inhibiting brake fluid additive and/or brake fluid replacement. For example, color swatches corresponding to copper levels below 200 ppm may be on a green field indicating that the use of a corrosion inhibiting brake fluid additive is appropriate, while color swatches corresponding to copper levels equal to or greater than 200 ppm may be on a red field indicating that the use of a corrosion inhibiting brake fluid additive is not recommended and brake fluid exchange is appropriate. Brackets, lines, and/or text may also be used to convey information about the recommended maintenance task (fluid OK, use additive, or replace fluid) based on copper level. FIG. 8 shows one example of an arrangement of lines 35 and text 36 for this information. Another copper level besides 200 ppm may be used as the threshold between additive use and fluid replacement. Another metal species besides copper may be used, with corresponding test strips, color chart, and threshold value.

Several methods of use will now be described for the corrosion inhibiting brake fluid additive, related kits, and for servicing brake fluid. These methods may also be applied to other vehicle fluid systems or other hydraulic systems.

Figure 9:
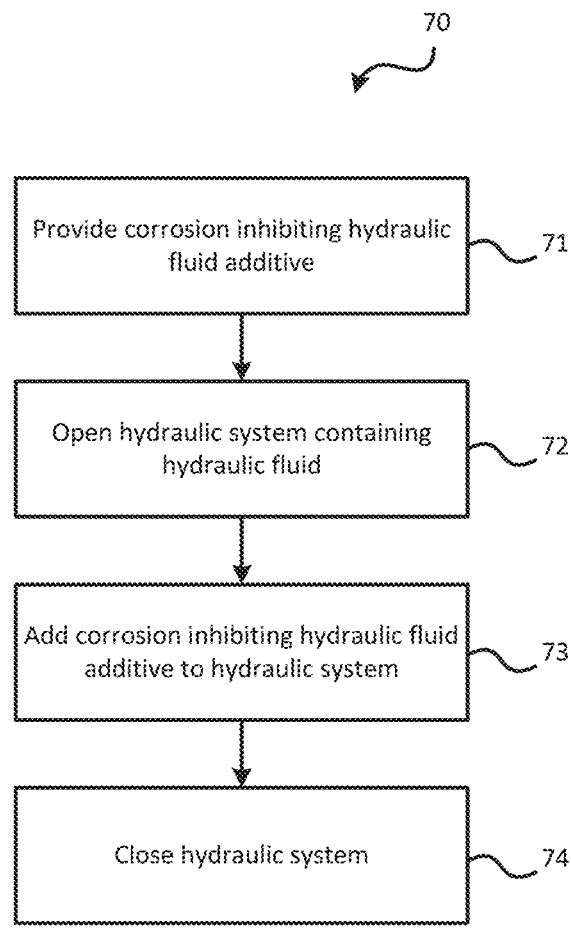
FIG. 9 is a flowchart diagram of a method of servicing a brake fluid.

Referring to FIG. 9, a first method 70 includes the steps of providing a corrosion inhibiting brake fluid additive 71, opening a brake system to access a brake fluid contained within 72, adding the corrosion inhibiting brake fluid additive 73, and closing the brake system 74.

The corrosion inhibiting brake fluid additive may be provided in the container 30, which may be part of a kit 31, 32, 33. The brake system may be opened by removing the brake fluid reservoir cap 64 or otherwise opening the master cylinder 52. The corrosion inhibiting brake fluid additive may be added to the brake system by pouring the additive into the brake fluid reservoir 53 or the master cylinder 52, for example, pouring the additive through a funnel. Alternatively, a syringe or injection device may be used to introduce the additive into the brake fluid reservoir 53, the master cylinder 52, or another location such as a bleed valve or a caliper bleed screw associated with a wheel or an ABS module. In order to add the corrosion inhibiting brake fluid additive to the brake fluid in the brake system, there may be one or more preceding steps of opening packaging, removing a lid or cap of the container 30, and/or removing or puncturing a seal (such as a tamper-evident or leak-proof seal) of the container 30. The brake system may be closed by replacing the brake fluid reservoir cap 64 or otherwise closing the master cylinder 52. In an optional step, a volume of brake fluid similar to the volume of corrosion inhibiting brake fluid additive may be removed or withdrawn from the brake system before adding the additive, to make room for the additive to avoid overfilling the brake system or overflow into the environment. The brake fluid may be withdrawn with a siphon, a syringe, suction, or through a bleed valve of the brake system.

This is only one of several possible methods whereby a brake fluid additive may be used to enhance the corrosion resistance of brake fluid. In other embodiments, rather than add the brake fluid additive directly to the brake system, used brake fluid may first be extracted from the brake system, and the brake fluid additive may then be added to the used brake fluid. The used brake fluid may be combined and mixed by any known mixing method. The used brake fluid with the additive may then be re-inserted into the brake system.

In other alternative embodiments, the brake fluid additive may be added to new (i.e., unused) brake fluid. The new brake fluid may or may not already include a corrosion resistant compound. In the case of new brake fluid with an existing corrosion-resisting component, adding the brake fluid additive of the present disclosure may supplement the operation of the existing corrosion-resisting component, thereby adding corrosion resistance beyond that provided by the existing corrosion-resisting component. In the case of brake fluid without an existing corrosion-resisting component, the brake fluid additive disclosed herein may serve as the sole corrosion-resisting component of the brake fluid.

Figure 10:
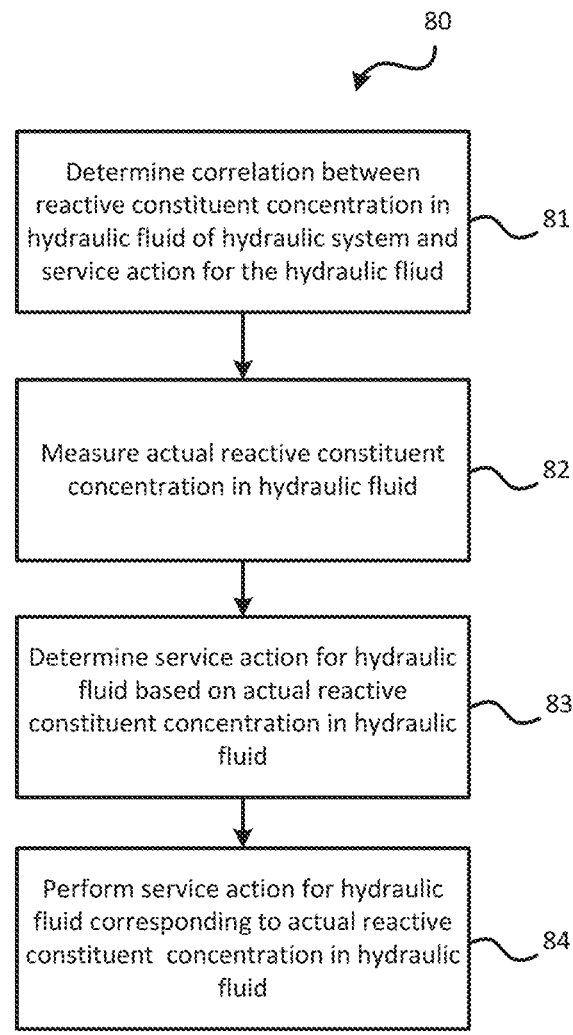
FIG. 10 is a flowchart diagram of another method of servicing a brake fluid.

Referring to FIG. 10, a second method 80 includes the steps of determining a correlation between a reactive constituent concentration in a brake fluid of a brake system and a service action for the brake fluid 81, measuring an actual reactive constituent concentration in the brake fluid 82, determining the corresponding service action for the brake fluid based on the actual reactive constituent concentration in the brake fluid 83, and performing the corresponding service action for the brake fluid corresponding to the actual reactive constituent concentration in the brake fluid 84.

The correlation between the reactive constituent concentration and the service action may establish one or more threshold values for reactive constituent concentration which correspond to service actions for the brake fluid. The reactive constituent may be copper, iron, zinc, tin, or aluminum. The service actions may include taking no action, adding a corrosion inhibiting brake fluid additive, and/or replacing the brake fluid. For example, if the copper concentration is 50 ppm or less, no service action may be necessary or recommended; if the copper concentration is greater than 50 ppm and less than 200 ppm, the corresponding service action may be to add the corrosion inhibiting brake fluid additive to the brake fluid using a method described previously herein; and if the copper concentration is greater than 200 ppm, the corresponding service action may be to replace the brake fluid. Other threshold values may be used. For instance, the fluid replacement threshold may be set at 175 ppm copper or 150 ppm copper instead of 200 ppm copper. The correlation may only address a subset of service actions. For example, the correlation may only address copper concentrations in the range between 50 ppm and 150 ppm, all of which may correspond to a single service action, which is to add the corrosion inhibiting brake fluid additive to the brake fluid.

The step of measuring the actual reactive constituent concentration in the brake fluid may be performed as described in U.S. Pat. No. 6,651,487 or U.S. Pat. No. 6,691,562. For example, measuring the copper level may include the step of exposing a copper reactive strip to the used brake fluid for reaction with copper in the used brake fluid. The step of measuring the actual reactive constituent concentration in the brake fluid may be performed on a sample of brake fluid contained in a brake fluid reservoir or master cylinder of a brake system, or a sample of brake fluid removed or withdrawn from a brake system reservoir, master cylinder, bleed valve, or the like.

The step of determining the corresponding service action for the brake fluid based on the actual reactive constituent concentration in the brake fluid may include comparing the actual reactive constituent concentration to a chart or other reference representing the correlation between copper concentration and service action. If the step of measuring the actual reactive constituent concentration was performed with a copper reactive strip, then the step of determining the corresponding service action may include comparing a resulting color on the exposed copper reactive strip to a color chart representing the correlation between color, copper concentration, and service action.

The step of performing the corresponding service action for the brake fluid corresponding to the actual reactive constituent concentration in the brake fluid may include taking no action, adding the corrosion inhibiting brake fluid additive to the brake fluid using a method previously described herein, such as the method of FIG. 9, or replacing the brake fluid.

The test results and recommended service actions outlined above are merely exemplary. In alternative embodiments, different service actions and/or no action may be recommended depending on the results of the test. For example, in some embodiments, there may be no threshold below which no service action is recommended. The use of the brake fluid additive disclosed herein may help resist future corrosion when added to brake fluid with none of the metal of interest (for example, no copper content), which may be new brake fluid as outlined above. Thus, the test may only have a high threshold (for example, 200 ppm) above which replacement of the brake fluid is recommended, and below which, addition of the additive is recommended (even with no copper content).

In addition to or in the alternative to having no lower threshold, the upper threshold also need not be used. For example, in some embodiments, it may be advantageous to add the brake fluid additive of the present disclosure even if there is an excessive quantity of the metal of interest (for example, over 200 PPM of copper) in the brake fluid. Although the presence of such a concentration of the metal of interest may be evidence of significant past corrosion, adding the brake fluid additive may help to inhibit future corrosion.

In some embodiments, the brake fluid additive may be added independently of testing. For example, if neither the lower threshold nor the upper threshold is used, as outlined above, the brake fluid may not need to be tested in order to recommend and/or implement one or more service actions. For example, the brake fluid additive may simply be added to the brake fluid as part of routine servicing. If desired, various criteria may be used to determine whether the brake fluid additive should be added. For example, addition of the brake fluid additive may depend on whether the brake fluid additive has not been added in connection with previous servicing, the length of time and/or number of miles driven since the last time the brake fluid was serviced, the amount of wear on the brake pads or other brake system components since the last time the brake system was serviced, and/or other factors. If desired, when the brake fluid additive is added, a tag, sticker, and/or other identifier may be placed on the master cylinder reservoir or in another visible location such as on the interior of the hood or on the firewall. Such a tag or other identifier may indicate the date the brake fluid additive was added, the quantity added, the measured concentration of copper in the brake system at the time the brake fluid additive was added, and/or any other information that may be useful for future diagnosis and/or servicing.

Figure 11:
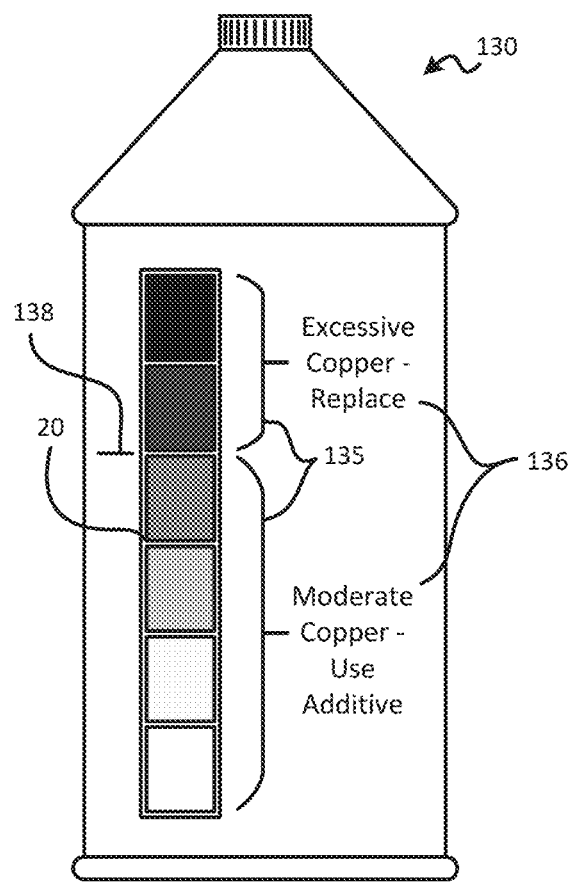
FIG. 11 is a side view of a container of corrosion inhibiting brake fluid additive according to one alternative embodiment.

Referring to FIG. 11, a side view illustrates a container 130 of corrosion inhibiting brake fluid additive according to one alternative embodiment. The container 130 may be used to carry out a method as described above, in which there is no lower threshold for addition of the brake fluid additive. The container 130 may be used in conjunction with one or more brake fluid test strips 10, and/or containers 40 of brake fluid test strips 10, as described in FIG. 8.

As shown, the container 130 may carry a color chart 20, as in FIG. 8. Further, the container 130 may have an arrangement of lines 135 and text 136 indicating recommended service actions, based on results of testing the hydraulic fluid. As shown, use of the additive may be recommended by the lines 135 and text, at any concentration of the metal of interest (for example, copper) up to an upper threshold 138. The upper threshold 138 may be, for example, 200 PPM. If the concentration of the metal of interest is higher than the upper threshold 138, the lines 135 and text 136 may recommend replacement of the hydraulic fluid.

In this application, "container" may be broadly interpreted to include any apparatus designed to hold, dispense, or otherwise retain test strips or fluid. Thus, a "container" may be a bottle, disposable package, dispenser, and/or any other apparatus that satisfies this definition. In some embodiments, a kit according to the present disclosure may include multiple containers. Some of these containers may reside within other containers. For example, a kit may have multiple bottles of brake fluid additive, multiple test strips, and/or one or more containers of test strips, all in a common package.

The concentration of copper is only one of many hydraulic fluid metrics that may be used to determine whether the hydraulic fluid is in need of servicing and/or replacement. In other alternative embodiments, testing may be carried out to obtain one or more other metrics pertinent to the hydraulic fluid, besides copper concentration. As mentioned previously, such a test may determine the concentration of a wide variety of metals, such as corrosion products, in the hydraulic fluid. However, the metrics tested need not relate to the concentration of a metal in the hydraulic fluid. Other fluid qualities, such as viscosity, appearance, pH, water content, and/or other metrics may be evaluated. Testing of pH will be shown and described in connection with FIG. 12.

Figure 12:
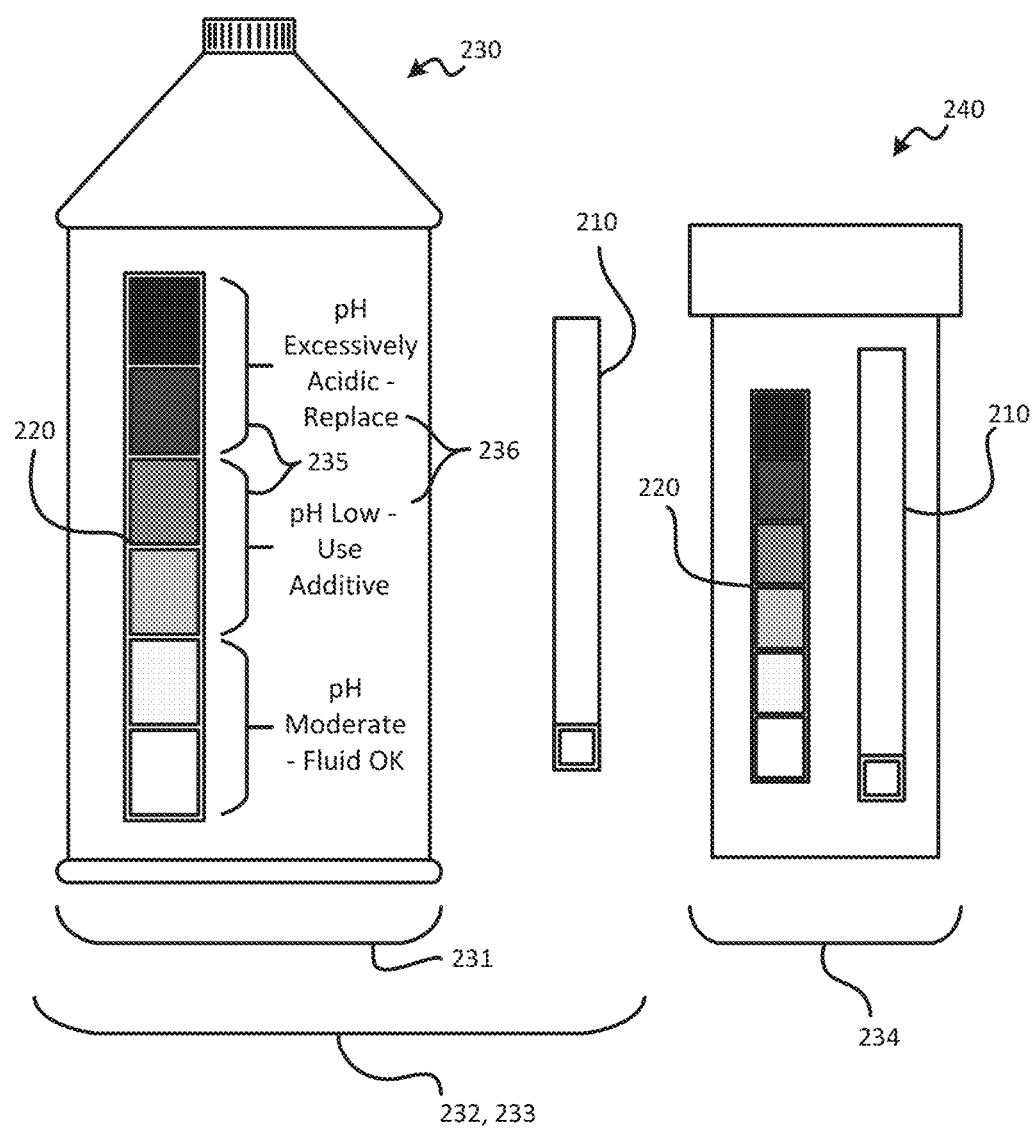
FIG. 12 is a side view of a container of corrosion inhibiting brake fluid additive according to another alternative embodiment.

Referring to FIG. 12, a side view illustrates a container 230 of corrosion inhibiting brake fluid additive, a brake fluid test strip 210, and a second container 240 of brake fluid test strips 210 according to one alternative embodiment. Like the container 30, the container 230 may hold, for example, one fluid ounce of the corrosion inhibiting brake fluid additive. Different container sizes may be provided for different brake systems.

The brake fluid test strips 210 may differ from the brake fluid test strips 10 of FIG. 8 in that the brake fluid test strips 210 may be designed to indicate the pH of the brake fluid, rather than indicating the concentration of Copper. The brake fluid test strips 210 may employ any known technique for indicating pH, many of which are known in the art. In some embodiments, each of the brake fluid test strips 210 may be designed adopt a color determined by the pH of the fluid sample being tested. This may occur, for example, after brief exposure of the fluid test strip 210 to used brake fluid and/or exposure to air for a predetermined amount of time. If desired, the brake fluid test strips 210 may be customized for use with brake fluid, and may thus be designed to provide colors or other indicators that accurately differentiate between the pH levels likely to be found in used brake fluid.

The container 230 may carry a color chart 220, as FIG. 12 shows. This arrangement may be referred to as a kit 231 which includes a container 230 of corrosion inhibiting brake fluid additive and a color standard, which may take the form of the color chart 220. As in the embodiment of FIG. 8, the color chart 220 may be carried in numerous ways, including on or in the container 230, on or in a different container, or independently of any container. The color chart 220 may differ from the color chart 20 of FIG. 8 in that the color chart 220 may be designed to help a user obtain the pH level of the brake fluid sample (either quantitatively or just qualitatively) by comparing the color chart with the brake fluid test strip 210. The color chart 220 is also shown carried on an exterior surface of the second container 240 in FIG. 12.

Any of the kits 232, 233, and/or 234 may be used in a manner similar to that set forth above, in the description of testing for the concentration of Copper in brake fluid. The test strip 210 may be exposed to the sample of brake fluid and/or other hydraulic fluid, and may then take on a color or other indicator corresponding to the pH level of the brake fluid. The test strip 210 may then be compared with the color chart 220 to obtain the pH level and/or recommended service action. As shown, lines 235 and text 236 indicate recommended service actions based on the results of comparison of the test strip 210 with the color chart 220. As in FIG. 8, the recommended service actions may include replacement of the brake fluid, addition of the brake fluid additive, and/or no action needed. Alternatively or additionally, any of these recommended service actions may be omitted, as in FIG. 11, or replaced with alternatives.

In some alternative embodiments, multiple testing methods may be used in conjunction with each other. For example, a kit (not shown) may include multiple types of tests, such as a test for the concentration of Copper (or another metal) and a test for pH or another brake fluid property. In some embodiments, the different test may be packaged and/or even applied together. For example, a container such as the container 30 and/or the container 40 of FIG. 8 may have a color chart 20 as in FIG. 8, which may be used to indicate a concentration of Copper, and a color chart 220 as in FIG. 12, which may be used to indicate pH. In some embodiments the tests may be administered together. For example, a single test strip may have multiple pads, including one pad that changes color or otherwise indicates the concentration of a metal of interest, and another pad that changes color or otherwise indicates the pH of the brake fluid. The test strip may be exposed to the brake fluid in such a manner that both pads are exposed to the brake fluid. The pads may then be used to determine the metal content, pH content, recommended service action(s), etc.

Such tests may be used together in various ways. According to some embodiments, the tests may provide independent recommendations. For example, a test for Copper concentration may provide a first recommended service action, and a test for pH level may provide a second recommended service action, which may not be the same as the first recommended service action. In some embodiments, the more conservative service action may be that which is ultimately recommended. For example, if the first recommended service action is to replace the brake fluid and the second recommended service action is to add the brake fluid additive, the composite recommended service action may be to replace the brake fluid. Similarly, if the first recommended service action is to take no action and the second recommended service action is to add the brake fluid additive, the brake fluid additive may be added. In alternative embodiments, a single recommended service action may be obtained by combining the results of the tests, for example, through the use of a weighted average or other mathematical formulation.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the disclosed technology.

While specific embodiments and applications of the present technology have been illustrated and described, it is to be understood that the claimed invention is not limited to the precise configuration and components disclosed herein. Various modifications, changes, combinations, and variations which will be apparent to those skilled in the art may be made in the arrangement, operation, and details of the methods and systems of the present technology disclosed herein without departing from the spirit and scope of the technology.

What is claimed is:

1. A method of testing hydraulic fluid in a hydraulic system, the method comprising the steps of:
    testing a sample of a hydraulic fluid, wherein the hydraulic fluid is in a hydraulic system;
    evaluating at least one test result to quantify a metric pertinent to the hydraulic fluid;
    based on the metric, determining that a corrosion inhibiting hydraulic fluid additive should be added to the hydraulic fluid; and
    in response to determining that the corrosion inhibiting hydraulic fluid additive should be added to the hydraulic fluid, adding the corrosion inhibiting hydraulic fluid additive to the hydraulic fluid without removing the hydraulic fluid from the hydraulic system;
    wherein the corrosion inhibiting brake fluid additive comprises a copper corrosion inhibitor comprising an organic compound comprising an azole.

2. The method of claim 1, wherein the hydraulic fluid is brake fluid and the hydraulic system is a brake system of a vehicle.

3. The method of claim 1, wherein the metric comprises a concentration of a metal of interest in the hydraulic fluid, wherein the metal of interest is selected from the group consisting of copper, iron, zinc, tin, and aluminum.

4. The method of claim 3, wherein the metal of interest is copper.

5. The method of claim 4, wherein quantify the metric comprises determining that the concentration of copper is greater than 50 parts per million.

6. The method of claim 4, wherein quantify the metric comprises determining that the concentration of copper is greater than 100 parts per million.

7. The method of claim 4, wherein quantify the metric comprises determining that the concentration of copper is greater than 150 parts per million.

8. The method of claim 1, wherein testing the sample of hydraulic fluid comprises exposing a reactive strip to the sample; and wherein evaluating at least one test result comprises comparing the reactive strip to a color standard representing a correlation between color and the metric.

9. The method of claim 1, wherein the corrosion inhibiting brake fluid additive comprises benzotriazole.

10. A method of treating hydraulic fluid of a hydraulic system, the method comprising:
    opening the hydraulic system;
    adding a hydraulic fluid additive to the hydraulic system;
    closing the hydraulic system to capture the hydraulic fluid and the hydraulic fluid additive; and
    in response to presence of the hydraulic fluid additive in the hydraulic fluid, inhibiting corrosion of the hydraulic system;
    wherein the hydraulic fluid comprises brake fluid and the hydraulic fluid additive is not suitable for use, alone, as brake fluid;
    wherein the hydraulic fluid additive comprises a copper corrosion inhibitor comprising an organic compound comprising an azole.

11. The method of claim 10, wherein the azole is benzotriazole.

12. The method of claim 11, wherein, after adding the hydraulic fluid additive to the hydraulic fluid, a mixture of the hydraulic fluid additive and the hydraulic fluid comprises 0.01% to 0.2% benzotriazole by weight.

13. The method of claim 10, wherein the hydraulic fluid additive comprises a volume of about 1 fluid ounce, with 0.45% benzotriazole by weight.

14. The method of claim 10, wherein the hydraulic fluid comprises new hydraulic fluid that has not yet been used in the course of operation of the hydraulic system, the method further comprising, after opening the hydraulic system and prior to closing the hydraulic system, adding the new hydraulic fluid to the hydraulic system.

15. The method of claim 10, wherein the hydraulic fluid comprises used hydraulic fluid that has been used in the course of operation of the hydraulic system, wherein opening the hydraulic system comprises obtaining access to the used hydraulic fluid, wherein adding the hydraulic fluid additive to the hydraulic system comprises adding the hydraulic fluid additive to the used hydraulic fluid.

16. The method of claim 15, further comprising prior to adding the hydraulic fluid additive to the hydraulic system:
    testing the used hydraulic fluid to obtain a measurement of a concentration of copper in the hydraulic fluid; and
    based on the measurement of the concentration of copper, determining that the hydraulic fluid additive is to be added to the hydraulic system.

17. The method of claim 16, wherein testing the used hydraulic fluid comprises the steps of:
    exposing a copper reactive strip to the used hydraulic fluid for reaction with copper in the used hydraulic fluid; and
    after exposure of the copper reactive strip to the used hydraulic fluid, comparing a color resulting on the copper reactive strip to a color standard representing a correlation between color and the concentration of copper.

* * * * *